United States Patent
Hong et al.

(10) Patent No.: US 11,471,867 B2
(45) Date of Patent: Oct. 18, 2022

(54) LIGAND FOR FORMING RUTHENIUM COMPLEX, RUTHENIUM COMPLEX CATALYST, PRODUCTION METHOD THEREFOR AND USE THEREOF

(71) Applicant: GWANGJU INSTITUTE OF SCIENCE AND TECHNOLOGY, Gwangju (KR)

(72) Inventors: Sukwon Hong, Gwangju (KR); Seunghwan Byun, Gwangju (KR)

(73) Assignee: Gwangju Institute of Science and Technology, Gwangju (KR)

( * ) Notice: Subject to any disclaimer, the term of this patent is extended or adjusted under 35 U.S.C. 154(b) by 367 days.

(21) Appl. No.: 16/609,197

(22) PCT Filed: Jun. 22, 2018

(86) PCT No.: PCT/KR2018/007122
§ 371 (c)(1),
(2) Date: Oct. 28, 2019

(87) PCT Pub. No.: WO2018/236191
PCT Pub. Date: Dec. 27, 2018

(65) Prior Publication Data
US 2020/0360911 A1    Nov. 19, 2020

Related U.S. Application Data

(60) Provisional application No. 62/523,803, filed on Jun. 23, 2017.

(51) Int. Cl.
*B01J 31/22* (2006.01)
*C07F 15/00* (2006.01)
(Continued)

(52) U.S. Cl.
CPC ....... *B01J 31/2278* (2013.01); *B01J 31/2226* (2013.01); *C07B 35/08* (2013.01);
(Continued)

(58) Field of Classification Search
CPC .. B01J 31/28; B01J 31/2265; B01J 1531/821; B01J 2231/543; C07F 15/0046; C07C 11/02
See application file for complete search history.

(56) References Cited

U.S. PATENT DOCUMENTS 6,635,768 B1 * 10/2003 Herrmann ............ B01J 31/2404
556/136
7,119,216 B2 * 10/2006 Newman ............... B01J 31/2273
554/162
(Continued)

FOREIGN PATENT DOCUMENTS

| CN | 104211735 A | 12/2014 |
| KR | 20150023672 A | 3/2015 |
| WO | 2011056881 A2 | 5/2011 |

OTHER PUBLICATIONS

Alcarazo, M.; Roseblade, S.J.; Cowley, A.R.; Fernandez, R.; Brown, J.M.; Lassaletta, J.M. J. Am. Chem. Soc. 2005, 127, 3290-3291. (Year: 2005).*

(Continued)

*Primary Examiner* — Rip A Lee
(74) *Attorney, Agent, or Firm* — Loza & Loza, LLP; Heidi Eisenhut

(57) ABSTRACT

The present invention relates to a novel ligand for forming a ruthenium complex, a ruthenium complex catalyst, a production method therefor and a use thereof. The ligand for forming a ruthenium complex and the ruthenium complex catalyst, according to the present invention, exhibit high catalytic activity, high selectivity, and stability.

13 Claims, 4 Drawing Sheets

(51) Int. Cl.
    *C08G 61/00*     (2006.01)
    *C07B 35/08*     (2006.01)
    *C08F 4/82*     (2006.01)

(52) U.S. Cl.
    CPC ............... *C07F 15/00* (2013.01); *C08F 4/82* (2013.01); *B01J 2231/005* (2013.01); *B01J 2231/12* (2013.01); *B01J 2231/543* (2013.01); *B01J 2531/004* (2013.01); *B01J 2531/821* (2013.01); *C07F 15/0046* (2013.01); *C08G 61/00* (2013.01)

(56) References Cited

U.S. PATENT DOCUMENTS

| | | | | |
|---|---|---|---|---|
| 7,960,599 | B2* | 6/2011 | Millis | C12P 7/6409 |
| | | | | 585/242 |
| 8,067,610 | B2* | 11/2011 | Schrodi | C07C 67/333 |
| | | | | 548/103 |
| 8,481,747 | B2* | 7/2013 | Schrodi | C07C 67/333 |
| | | | | 548/103 |
| 8,809,563 | B2* | 8/2014 | Holtcamp | C07C 6/04 |
| | | | | 585/639 |
| 9,120,742 | B2* | 9/2015 | Abraham | C07C 67/475 |
| 9,249,170 | B2* | 2/2016 | Marx | C07C 6/04 |
| 2019/0291089 | A1* | 9/2019 | Skowerski | C07C 67/475 |
| 2021/0291155 | A1* | 9/2021 | Herron | B01J 31/226 |

OTHER PUBLICATIONS

Pazio et al., "Nitrenium ions and trivalent boron ligands as analogues of N-heterocyclic carbenes in olefin metathesis: a computational study" in Dalton Transactions, Issue 46, 2015, The Royal Society of Chemistry. (9 pages).

Bouffard et al., "Synthesis of Highly Stable 1,3-Diaryl-1H-1,2,3-triazol-5-ylidenes and Their Applications in Ruthenium-Catalyzed Olefin Metathesis" in Organometallics 2011 30 (9), American Chemical Society, pp. 2617-2627. DOI: 10.1021/om200272m . (24 pages).

PCT/KR2018/007122. International Search Report & Written Opinion dated Oct. 16, 2018. (12 pages).

Schrodi et al. "Ruthenium olefin metathesis catalysts for the ethenolysis of renewable feedstocks." Clean vol. 36(8), pp. 669-673 (Aug. 2008).

Marx et al. "Cyclic alkyl amino carbene (CAAC) ruthenium complexes as remarkably active catalysts for ethenolysis." Renewable Carbon Sources Hot Paper Angew. Chem. Int. Ed. 54, pp. 1919-1923 (2015).

Vougioukalakis et al. "Ruthenium-based heterocyclic carbene-coordinated olefin metathesis catalysts." Chem. Rev. 2010, 110, 1746-1787 (Dec. 14, 2009).

Hong et al. "Decomposition of ruthenium olefin metathesis catalysts." J. Am. Chem. Soc., 129:25, 7961-7968 (Jun. 5, 2007).

Alcarazo et al. "Imidazo[1,5-a]pyridine: A Versatile Architecture for Stable N-Heterocyclic Carbenes." J. Am. Chem. Soc. vol. 127, pp. 3290-3291 (Feb. 17, 2005).

* cited by examiner

LIGAND FOR FORMING RUTHENIUM COMPLEX, RUTHENIUM COMPLEX CATALYST, PRODUCTION METHOD THEREFOR AND USE THEREOF

TECHNICAL FIELD

The present disclosure relates to a ligand for ruthenium complex formation, a ruthenium complex catalyst, a preparation method thereof, and use thereof.

BACKGROUND ART

A following shell higher olefin process (SHOP) is a method of synthesis of linear α-olefin obtained from petrochemical raw materials as developed in 1977.

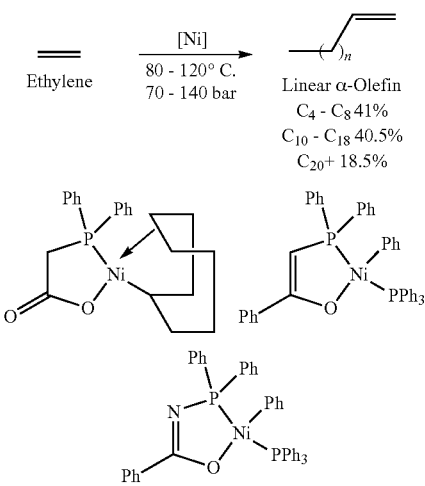

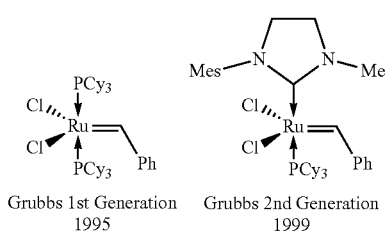

The shell higher olefin process has a problem in that the linear α-olefin has a wide distribution such that 41% of 4 to 8 carbon atoms, 40.5% of 10 to 18 carbon atoms and 18.5% of 20 or greater carbon atoms are obtained. For example, the shell higher olefin process has a low synthesis yield of 1-decene. In addition, this SHOP requires a high temperature of 60 to 300 degrees C. and a high pressure of 30 to 200 bar.

In order to overcome these drawbacks, research and development of ruthenium complex catalysts in olefin metathesis is vigorous.

Known ruthenium complex catalysts include the 2005 Nobel Prize-winning Grubbs catalyst (Yves Chauvin, Robert H. Grubbs and Richard R. Schrock).

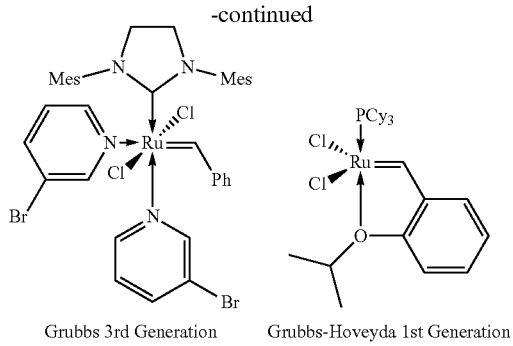

Grubbs 3rd Generation 2001

Grubbs-Hoveyda 1st Generation 1999

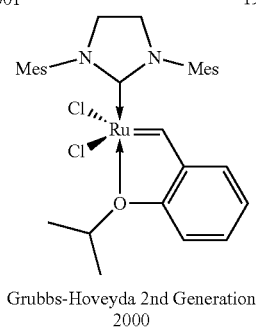

Grubbs-Hoveyda 2nd Generation 2000

For the production of linear α-olefin, natural seed oils may be used instead of petroleum based raw material.

For example, a method for synthesizing a linear α-olefin obtained from a renewable seed oil raw material is as follows.

Methyl oleate may undergo cross metathesis with ethylene. C=C double bond is decomposed by ethenolysis of the methyl oleate. Thus, the desired linear α-olefin may be synthesized.

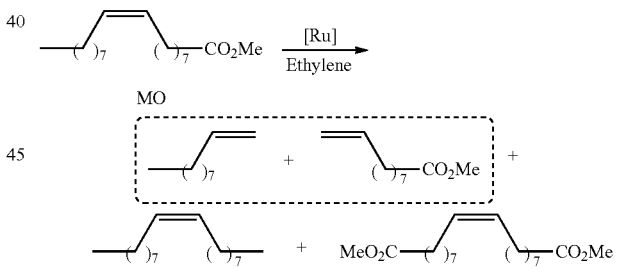

Unlike the SHOP (Shell Higher Olefin Process) as described above, the synthesis yield of a single 1-decene is high in this cross metathesis. Further, unlike the SHOP (Shell Higher Olefin Process) as described above, the cross metathesis reaction using the Ru catalyst has an advantage that the reaction may be carried out under a low temperature of 40° C. to 100° C. and a low pressure of about 10 bar.

Further, the ruthenium complex catalyst may be N-heterocyclic carbene (NHC) ligand. Since the ruthenium complex with asymmetrically substituted N-heterocyclic carbene ligands exhibits a high selectivity to a cross-metathesis product compared to a by-product from the self-metathesis, the ruthenium complex with asymmetrically substituted N-heterocyclic carbene ligands has been identified as a promising catalyst for ethenolysis (Yann Schrodi, Thay Ung, Angel Vargas, Garik Mkrtumyan, ChoonWoo Lee, Timothy M. Champagne, Richard L. Pederson, Soon Hyeok Hong_Clean: Soil, Air, Water, 2008, 36, 669). Stabilization of methylidene intermediates has been suggested as a key factor in improving catalyst activity. It is known that additional electron donating ligands can help stabilize these methylidene intermediates (Vanessa M. Marx, Alexandra H. Sullivan, Mohand Melaimi, Scott C. Virgil, Benjamin K. Keitz, David S. Weinberger, Guy Bertrand, and Robert H. Grubbs_Angew. Chem. Int. Ed. 2015, 54, 1919).

The stability of the methylidene species was compared.

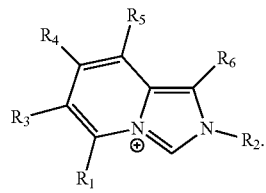

[Chemical Formula 1a]

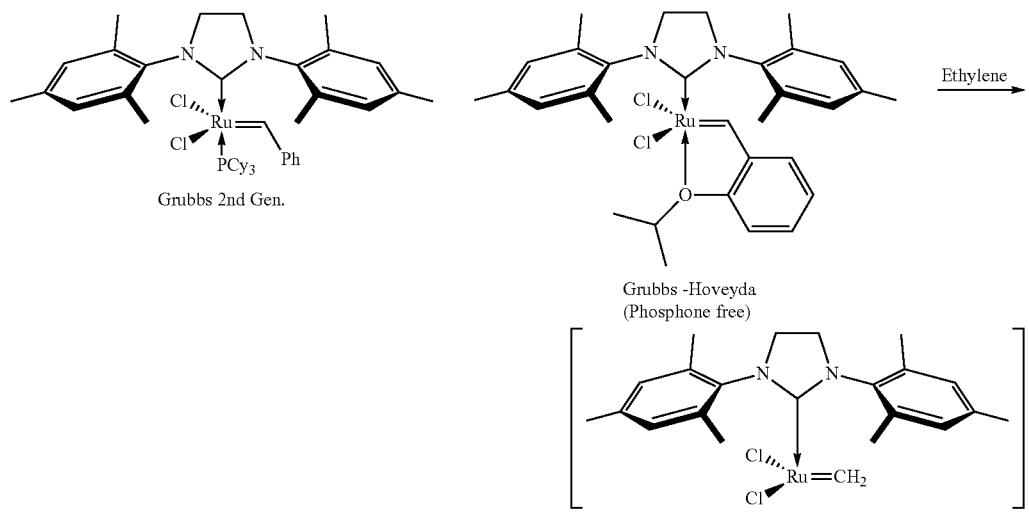

However, a phosphine ligand (Soon Hyeok Hong, Anna G. Wenzel, Tina T. Salguero, Michael W. Day, and Robert H. Grubbs_J. Am. Chem. Soc. 2007, 129, 7961) is degraded by phosphine. Thus, the phosphine-free catalyst is more stable than the phosphine ligand. Accordingly, the present inventors have studied the phosphine-free catalyst having the stability.

Imidazo [1,5-a]pyridine-3-ylidene (mPy), which was first reported in 2005, is a candidate for a structurally asymmetric NHC ligand and has various electronic characteristics.

Thus, the present inventors have repeatedly studied the effect of the asymmetric Impy-based ligand structure change on the activity, selectivity and stability of the catalyst. We have acquired a novel ruthenium complex ligand and ruthenium complex which has a high activity as a catalyst, and has a high selectivity to formation of terminal olefins in ethenolysis of methyl oleate and has high stability.

DISCLOSURE

Technical Purposes

A purpose of the present disclosure is to provide a novel ruthenium complex ligand and ruthenium complex which has a high activity as a catalyst, and has a high selectivity to formation of terminal olefins in ethenolysis of methyl oleate and has high stability.

Technical Solutions

A ligand for the ruthenium complex formation in accordance with the present disclosure has a following Chemical Formula:

A ruthenium complex catalyst according to the present disclosure has a following Chemical Formula:

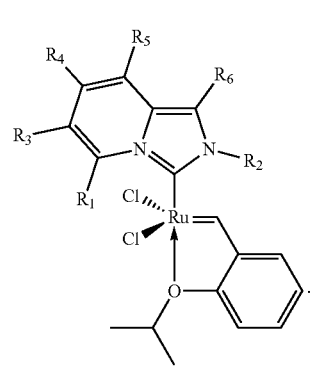

[Chemical Formula 2a]

Technical Effects

The ruthenium complex catalyst for ruthenium complex formation according to the present disclosure have the high catalyst activity, high selectivity, and stability.

The ruthenium complex catalyst according to the present disclosure can exhibit the high selectivity to the formation of terminal olefins in the ethenolysis of methyl oleate. As a result, the production efficiency of the terminal olefin can be improved.

DETAILED DESCRIPTIONS

Figure 1:
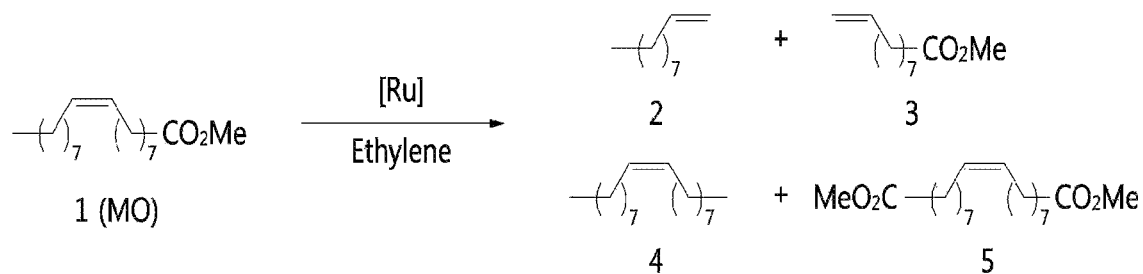
FIG. 1 shows ethenolysis of methyl oleate and ruthenium metathesis catalyst.
Figure 1:
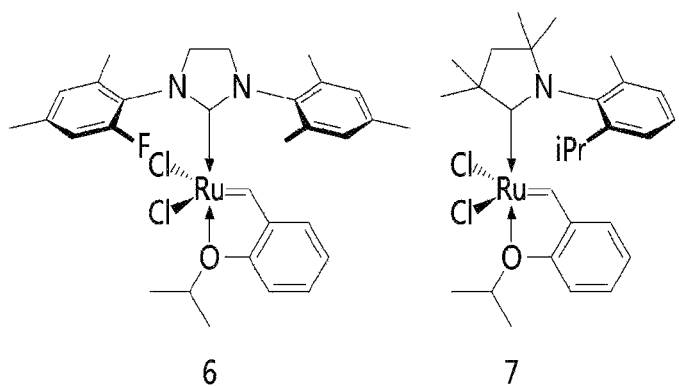
Figure 1:
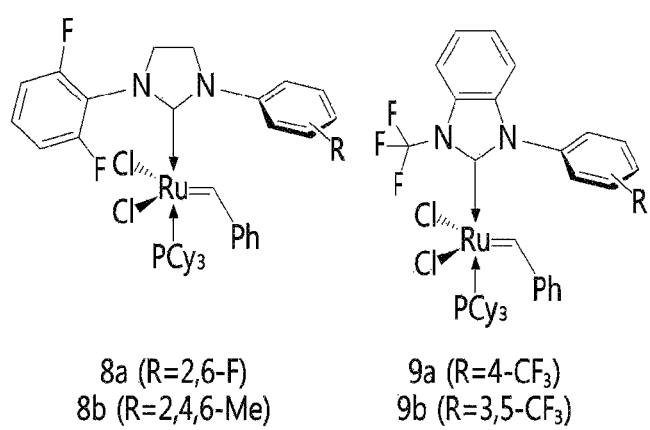
Figure 1:
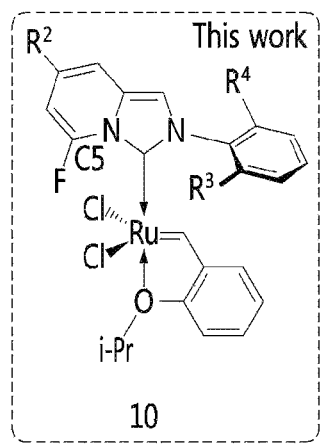

The present disclosure is described in more detail below.

The present inventors have considered that the ruthenium complex with asymmetrically substituted N-heterocyclic carbene ligand exhibits a high selectivity to the cross-metathesis product compared to the by-products from self-metathesis. In conjunction with this consideration, we have studied the asymmetric ImPy-ruthenium complex catalysts.

Thus, the present inventors have completed a ligand for ruthenium complex formation, the ligand having following [Chemical Formula 1a] and [Chemical Formula 1b].

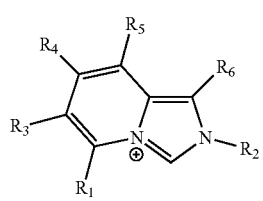

[Chemical Formula 1a]

The ligand for ruthenium complex formation with a structure of the Chemical Formula 1a according to the present disclosure may include an asymmetric structure. In this connection, the asymmetric structure may mean that sizes of R1 and R2 are different from each other. In detail, R1 may include an atom or an atomic group smaller than that of R2. In the Chemical Formula 1a, due to the asymmetric structure where R1 has a smaller size than R2, the ligand for ruthenium complex formation with a structure of the Chemical Formula 1a may have the high selectivity. In this connection, the selectivity may mean that a proportion of the cross-metathesis product is higher than a portion of the by-product from the self-metathesis. Thus, the ligand for ruthenium complex formation according to the Chemical Formula 1a may bind with the ruthenium to be used as a catalyst for ethenolysis.

In the ligand for ruthenium complex formation with the structure according to Chemical Formula 1a, R1 and R2 may electronically and/or sterically influence the ruthenium since R1 and R2 may be placed at a close distance from the ruthenium atom or the atomic group bonded to ruthenium. Thus, in the ligand for ruthenium complex formation with a structure according to Chemical Formula Ia, R1 and R2 were determined under electronic and stereo control.

R1 may be F or methyl. The halogen element other than F increases the bond length with cyclic carbon and the size of the element is large and thus has the increased steric repulsion, to lower the selectivity of the reaction. Further, alkyl groups other than methyl may have the increased steric repulsion during ruthenium complex catalyst formation, thereby to reduce the selectivity of the reaction.

R2 may include substituted or unsubstituted aryl. For example, R2 may comprise a substituted aryl of 9 to 12 carbon atoms.

Each of R3, R4, R5 and R6 may represent one selected from a group consisting of hydrogen, a halogen atom, a linear or branched alkyl group having 1 to 5 carbon atoms, or an alkoxy group having 1 to 5 carbon atoms. For example, each of R3, R5, and R6 may include hydrogen. For example, R4 may include one selected from a group consisting of H, t-Bu, MeO, and Cl.

The structure of R2 will be described in detail with reference to a following Chemical Formula 1b:

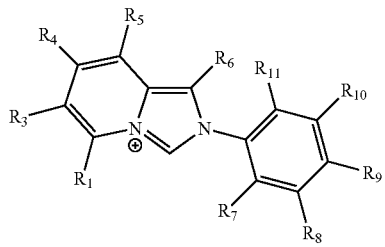

[Chemical Formula 1b]

In the Chemical Formula 1b, each of R1, R3, R4, R5, and R6 are the same as in Chemical Formula 1a described above.

Each of R7, R8, R9, R10, and R11 may be selected from a group consisting of hydrogen or a linear or branched alkyl group having 1 to 8 carbon atoms. For example, each of R7, R8, R9, R10, and R11 may include one selected from hydrogen or a linear or branched alkyl group having 1 to 4 carbon atoms.

For example, R7 may include any one selected from ethyl, isopropyl, and t-butyl. For example, each of R8, R9, and R10 may include hydrogen. For example, R11 may be any one selected from methyl, ethyl, and isopropyl.

In the Chemical Formula 1b, R7 and R11 may have the same or different substituents. Specifically, the carbon number of R7 may be the same as the carbon number of R11, or the carbon number of R7 may be larger than the carbon number of R11. In one example, R7 and R11 may each be isopropyl. Alternatively, R7 and R11 may each be ethyl. In one example, R7 may be ethyl and R11 may be methyl. Alternatively, R7 may be isopropyl and R11 may be hydrogen. Alternatively, R7 may be t-butyl and R11 may be hydrogen.

Further, the present The inventor completed a ruthenium complex catalyst with [Chemical Formula 2a] and [Chemical Formula 2b]. The ruthenium complex catalyst with [Chemical Formula 2a] and [Chemical Formula 2b] may be formed by combining the ruthenium with the ligand for the ruthenium complex formation having the structure of [Chemical Formula 1a] and [Chemical Formula 1b]:

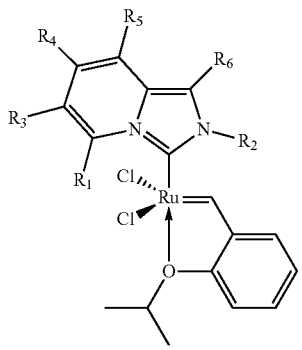

[Chemical Formula 2a]

Since the ruthenium complex catalyst of the Chemical Formula 2a is a phosphine-free complex, instability due to decomposition may be removed. Further, the ruthenium complex catalyst of the Chemical Formula 2a is stable because R1 of the heterobicyclic ligand containing nitrogen can form a stable coordination with a metal center of Ru.

In the Chemical Formula 2a, R1, R3, R4, R5, and R6 are the same as in the Chemical Formula 1a as described above.

The structure of R2 will be described in detail with reference to the following Chemical Formula 2b:

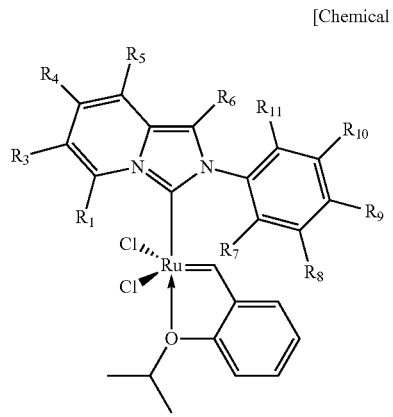

[Chemical Formula 2b]

In the Chemical Formula 2b, R7, R8, R9, R10 and R11 are the same as described above with reference to the Chemical Formula 1b.

More specifically, the present disclosure is described in detail below.

A cross-metathesis reaction with ethylene known as ethenolysis, has recently attracted much attention in terms of the selective synthesis of terminal olefins from renewable seed oils.

Referring to FIG. 1, we describe the ethenolysis reaction using a ruthenium catalyst.

The ethylene-based metathesis reaction is also called ethenolysis, and refers to a reaction that decomposes internal olefins to be converted to terminal olefin groups. This reaction has also been proposed as a new method for producing linear alpha olefins from oils present in nature, not via the petrochemistry. The present inventors have studied the reaction conversion, selectivity and catalyst reactivity using the methyl oleate.

In detail, we describe the ethenolysis of methyl oleate (1) and ruthenium metathesis catalyst.

Terminal olefins (so-called linear alpha-olefins; 2 and 3 in FIG. 1) may act as important building blocks for various chemicals. The ruthenium complex with the N-heterocyclic carbene (NHC) ligand may be selected as one of the catalysts for ethenolysis.

Recent studies are focusing on the structural variation of the NHC ligand in order to achieve the selectivity to the desired α-olefins (2 and 3 in FIG. 1) higher than that of the self-metathesis by-products (4 and 5 in FIG. 1) thereto and to improve the reaction efficiency.

The Grubbs-Hoveyda second-generation catalyst (6 in FIG. 1) mediates ethenolysis of methyl oleate (MO, 1), and exhibits 33% selectivity, 20% yield, and a turnover number of 2000 at 100 ppm catalyst loading. Stabilization of methylidene intermediates is known to play a pivotal role in ensuring the high turnover number and selectivity in the ethenolysis of methyl oleate.

In the ruthenium complex catalyst, the three-dimensional asymmetric substitution pattern of the N-heterocyclic carbene (NHC) ligand has been found to be very important for α-olefin selective ethenolysis. The lack of stereoscopic interactions on one side may favor "non-productive" metathesis of the alpha-olefin product and the methylidene intermediate to regenerate the same methylidene intermediate.

Imidazo[1,5-a]pyridin-3-ylidene carbine (ImPy), which was first reported independently by JM Lassaletta and F. Glorius in 2005, is a bicyclic variant of a typical imidazoylidene NHC. The ImPy ligand has an inherently asymmetric structure and is known to carry more electron donors than imidazolyliden NHC. Thus, the present inventors thought that the Ru-ImPy catalyst could be a good candidate for an efficient and selective ethenolysis reaction. Further, the R1 substituent of ImPy may be located close to the Ru metal center. For example, when R1 is fluorine, the Ru—F distance is expected to be short enough in terms of Ru—F bond interactions, which is not the case for other ruthenium metathesis catalysts with fluorinated NHC. The ImPy ligand (ImPy-Ru, 10) and ruthenium complex have not been reported.

Figure 2:
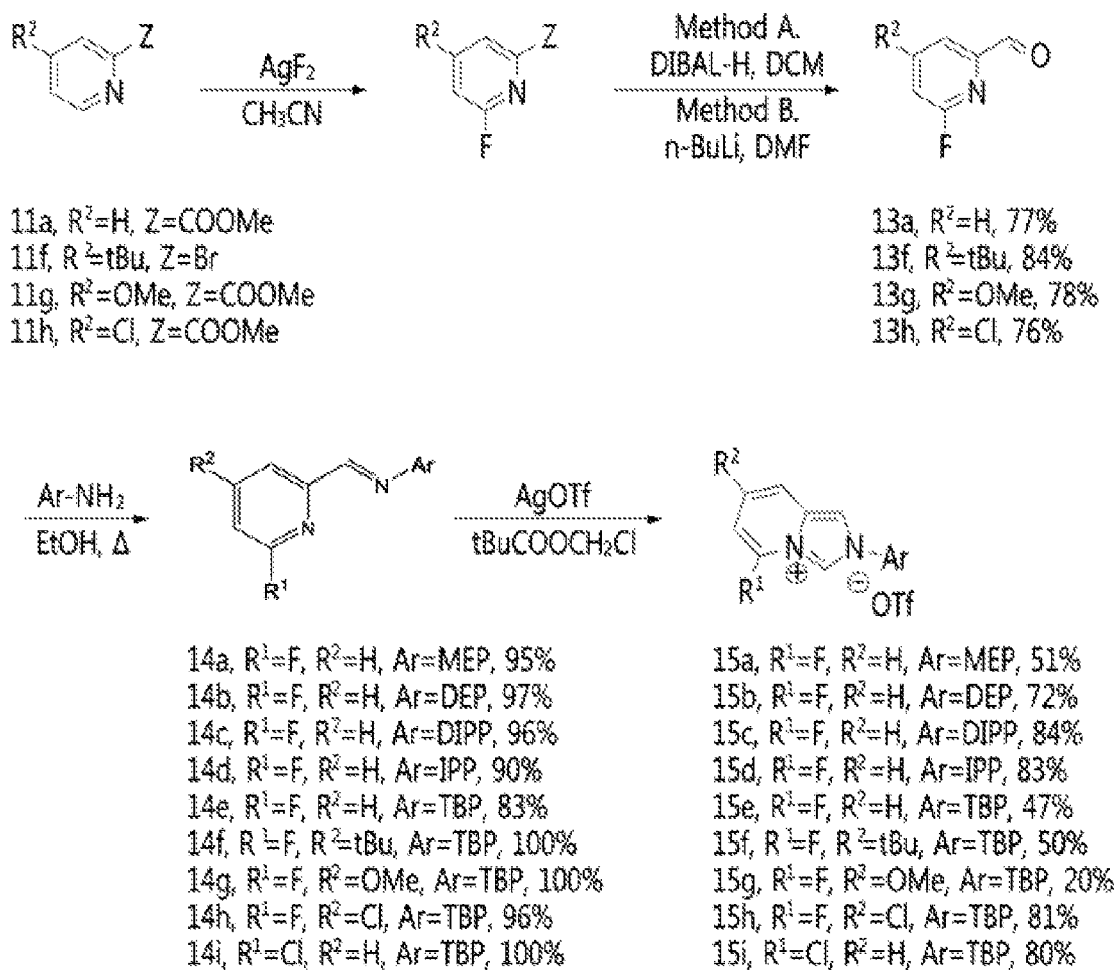
FIG. 2 shows synthesis of a ligand precursor according to an embodiment.

In a following description, we refer to FIG. 2 to explain the synthesis of the ruthenium complex with a fluorinated asymmetric ImPy ligand (15), and changing of substituents on both the backbone of the ligand and the nitrogen atom, and an application thereof to the ethenolysis of methyl oleate. The ImPy-Ru catalyst exhibits a high selectivity (74% to 86%) for terminal olefin formation in ethenolysis of methyl oleate (MO).

FIG. 2 shows establishment of conditions for the synthesis of Ethenolysis ruthenium catalyst. In detail, FIG. 2 shows N-heterocyclic carbene (NHC) ligand synthesis. More specifically, a ligand based on an imidazopyridine structure, not based on the basic imidazole structure of the NHC, can be readily synthesized using the Glorius or Aron method. In this method, fluorine, chlorine, and methyl functional groups may be input to into R1, and tertiary butyl, methoxy, chlorine functional groups may be introduced to R2 to control electrical properties of the ligand. Then, using N—Ar containing various alkyl groups, ligands 15a, 15b, 15c, 15d, 15e, 15f, 15g, 15h and 15i various steric restrictions can be synthesized.

FIG. 2 is a simplified representation of the synthesis of ligand precursors of 15a to 15h. 2-fluoropyridine derivatives (12a, 12f, 12g and 12h) were synthesized by selective fluorination using $AgF_2$ in $CH_3CN$ according to well-known procedures in the field of the present disclosure (Refer to P. S. Fier and J. F. Hartwig, Science 2013, 342, 956).

DIBAL-H reduction of 2-pyridinecarboxylate derivatives (12a, 12g and 12h) yielded fluoropyridine carboxaldehyde (13a, 13g and 13h) with good separation yield. Alternatively, lithiation of 2-bromobipyridine (12f) followed by reaction with DMF yielded fluoropyridine carboxaldehyde (13f).

Next, imine formation (14a-14i) with aniline followed by cyclization with AgORf and chloromethyl pivalate provided the ImPy ligand with good overall separation yield (Christian Burstein, Christian W. Lehmann and Frank Glorius, Tetrahedron, 2005, 61, 6207).

ImPy containing chlorine atoms and methyl groups (10i to 10k) was synthesized from 6-chloropyridinecarboxaldehyde (13i, SI) and 6-methylpicolinecarboxaldehyde (13k, SI).

Figure 3:
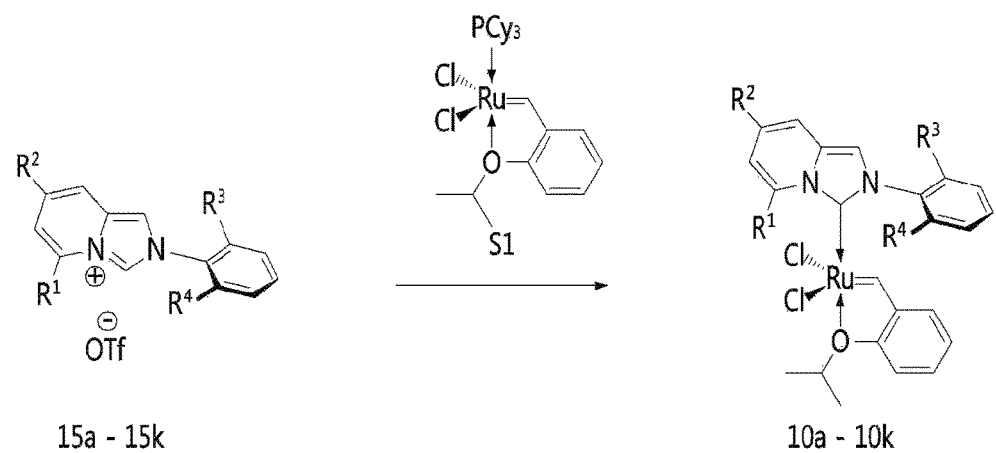
FIG. 3 shows synthesis of various ImPy-Ru complexes according to an embodiment.
Figure 3:
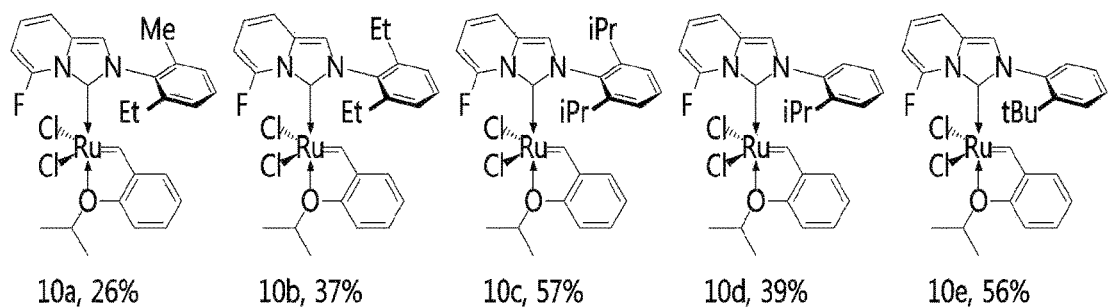
Figure 3:
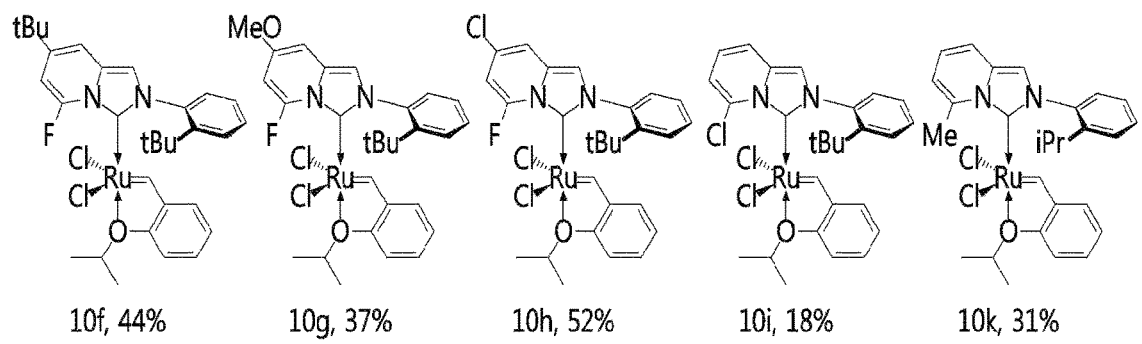

FIG. 3 shows synthesis (isolated yield) of the ImPy-Ru complex. The following description will be made with reference to FIG. 3.

The Ru catalysts (10b, 10c, 10d, 10e, 10f, 10h, 10i, 10h, and 10k) were synthesized by the exchange reaction between free carbene made with the base and the phosphine ligand of the first generation Grubbs-Hoveyda catalyst.

The ImPy-Ru complex was synthesized as follows with the fluorinated ImPy ligand precursor (15a-15h). After in-situ deprotonation of imidacopyridinium salts (15a-15h) using potassium hexamethyldisilazide (KHMDS), the resulting product reacts with RuCl2(PCy$^3$)(=CH-o-O$^i$PrC$_6$H$_4$)(S1) to produce Grubbs-Hoveyda-type Ru complex with the ImPy ligand (10a-10k) at a reasonable separation yield ((a) S. F. Monsaert, F. W. C. Verpoort, Eur. Pat. 300 2011091980, 2011; S. F. Monsaert, F. W. C. Verpoort, WO 2011/091980 A1; S. F. Monsaert, F. W. C. Verpoort, PCT/EP2011/000300, 2011, (b) B. J. van Lierop, A. M. Reckling, J. A. M. Lummiss, and D. E. Fogg, ChemCatChem 2012, 4, 2020).

Complex (10i) containing a chlorine atom instead of fluorine was synthesized in a similar manner. These chelated benzylidene complexes (10a-10k) are stable under atmospheric conditions (air and moisture). These complexes were characterized by nuclear magnetic resonance spectroscopy (NMR), high resolution mass spectrometry (HRMS) and X-ray crystallography. The single crystal suitable for X-ray crystallography was grown by slow diffusion of hexane through the catalyst solution in dichloromethane at 25° C.

Figure 4:
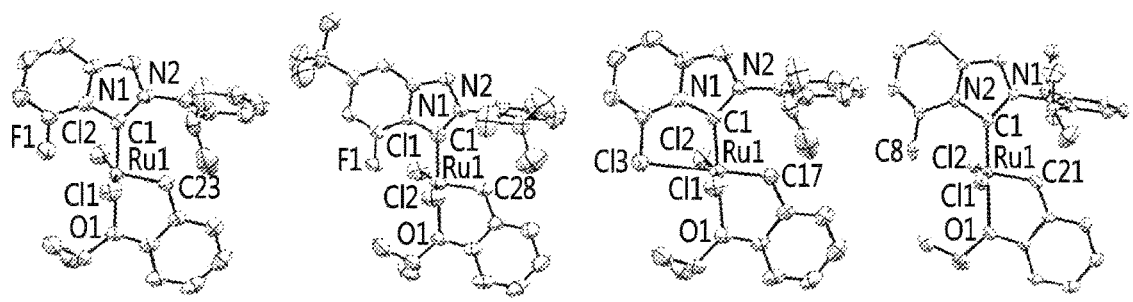
FIG. 4 shows a solid-phase structure by X-ray analysis of various ImPy-Ru complexes according to an embodiment.

FIG. 4 shows the solid-phase structure by X-ray analysis of various ImPy-Ru catalyst single crystals according to an embodiment. For clarity, the representation of hydrogen atoms is omitted.

Among the synthesized catalysts, 10f (the second structure from the left in FIG. 4) and 10i (the third structure from the left in FIG. 4) were grown into a single crystal, and then the crystal structure analysis thereof confirmed that the expected catalyst was synthesized.

Ru—F interactions may be identified on solid phase from X-ray analysis. The Ru—F interactions are believed to be involved in stabilizing the ruthenium methylidene intermediates.

Referring to FIG. 4, the solid-phase analysis shows that the complex showing the orientation of the twisted tetragonal pyramidal shape and the N-aryl group are located on the O-chelated benzylidene. The ImPy-Ru catalysts are structurally similar to NHC carrying ruthenium catalyst. The R1 group (especially the fluorine atom) is positioned next to the ruthenium metal center. This is not the case for other ruthenium metathesis catalysts with fluorinated NHC ((a) T. Ritter, M. W. Day, and R. H. Grubbs, J. Am. Chem. Soc. 2006, 128, 11768-11768, (b) P. S. Engl, A. Fedorov, C. Coperet, and A. Togni, Organometallics 2016, 35, 887-893). The ruthenium-fluorine interaction may be due to an appropriate Ru—F distance for 10c (Ru—F1=2.688 (3)), and 10f (Ru—F1=2.700 (3)). The ImPy ligand containing the chlorine atom may be well coordinated with ruthenium, as determined based on the Ru—Cl distance for 10j (Ru—Cl3=2.7194 (8)). Because the methyl group is sterically larger than the chloride and fluorine atoms, the Ru—C8 distance (Ru—C8=2.925 (3)) in Me-ImPy (101) is much larger than that of F-ImPy (10c and 10f) and Cl-ImPy (10j).

The selected coupling length (A) and coupling angle (°) are as follows.

For 10c: Ru—C1=1.956(5)A, Ru=C19=1.822(5)A, Ru—F1=2.688(3) A, Ru—O(1)=2.282(3)A, N1-C1-N1=101.8(3)°, C11-Ru—C12=154.13(5)°,

For 10f: Ru—C1=1.972(5)A, Ru=C28=1.803(5)A, Ru—F1=2.700(3) A, Ru—O1=2.274(3)A, N1-C1-N2=102.4(4)°, C11-Ru—C12=155.13(6)°,

For 10j: Ru—C1=1.967(3)A, Ru=C17=1.840(3)A, Ru—C13=2.7194(8)A, Ru—O1=2.294(2)A, N1-C1-N2=102.0(2)°, C11-Ru—C12=165.43(3)°,

For 101: Ru—C1=1.972(4)A, Ru=C21=1.831(3)A, Ru—C8=2.925(3)A, Ru—O1=2.300(3)A, N1-C1-N2=101.4(3)°, C11-Ru—C12=162.32(4)°.

Hereinafter, the present disclosure will be described in more detail through a concrete example.

The catalyst performance of the prepared ImPy-Ru complex was evaluated in the methyl oleate ethenolysis reaction.

The evaluation results are shown in Table 1.

Initial results in 10c (item 3) show that the structural asymmetry of the ImPy ligand results in an alpha-olefin selectivity, compared to the selectivity exhibited by other Grubbs-Hoveyda type Ru catalysts containing symmetric NHC. To investigate the steric effect of the ImPy ligand, the F-ImPy-Ru complexes (10a-10e and 10k) was tested in terms of ethenolysis reaction, using 100 ppm catalyst thereof at 60° C. and 150 psi ethylene. The complexes 10a and 10b show the higher conversion and turnover number compared to the complex 10c. However, probably because the steric hindrance is reduced on the same side, the complexes 10a and 10b exhibited a lower selectivity to the end products (2 and 3) compared to the products (4 and 5) of the self- and secondary-metathesis reactions (items 1, 2 and 3 in the table 1).

Control of the steric bulk of the same-side N-aryl group results in higher selectivity in ethenolysis. The use of mono-ortho-substituted N-aryl groups (10d and 10e) improved the turnover number to 2200 and 3400 while maintaining a high selectivity of 82% and 79% (items 4 and 5).

When the mono-ortho-substituted N-aryl groups are used, there may be a space for coordination of the olefins. A larger ortho substituent appears to be better for overall catalyst efficiency (R4=t-Bu vs i-Pr) when a mono-substituted aryl (R3=H) is used.

In Me-ImPy-Ru (10k), 91% selectivity was obtained, but the turnover number was lower presumably due to increased steric hindrance (item 6).

The present inventors compared the activities of synthesized ruthenium complex catalysts with each other. The results of the activity analysis of the ruthenium complex catalysts indicated by 10a to 10k having different structures are shown in Table 1.

The effects from steric restrictions of various alkyls having N-aryl groups were compared and analyzed using the synthesized catalysts 10a to 10k at a 100 ppm content at 60° C. for 3 hours.

The complexes 10a and 10b showed higher conversion compared to the complex 10c. However, both the former catalysts showed the lower selectivity because of the reduced steric restrictions of the alkyl having the N-aryl group. The larger the steric restrictions of the alkyl having the N-aryl group, the higher the selectivity.

The complexes 10d and 10e showed higher conversion compared to the complex 10c and at the same time maintained high selectivity. This is presumably due to the fact that there is a proper space for the olefin access when the alkyl is substituted only into one ortho-site in the N-aryl group.

Therefore, when the N-aryl group has a large alkyl group at the ortho position, this exhibits better catalyst conversion. The 10k has the high selectivity as in the above catalysts satisfying the above conditions, but the catalyst efficiency of the 10k is low. This is expected due to the steric restriction of the methyl group of R1.

The reaction conditions in the experiment in Table 1 were based on the catalyst content (ppm), and $C_2H_4$(150 psi, 99.95% purity). The conversion and selectivity at 60° C. for 3 hours were measured using tridecane as an internal standard and using GC.

The conversion is calculated as 100−[(final molar number 1)*100/[initial molar number 1]].

The selectivity is calculated as 100*(2+3 moles)/[(2+3 moles)+(2*4+5 moles)].

The yield is calculated as conversion*selectivity/100.

The turnover number is calculated as yield*(initial mole number 1/mole number of catalyst)/100.

TABLE 1

Ethenolysis of methyl oleate using sterically different catalysts (10a-10e, 10k)

| Item | Catalyst | Loading (ppm) | Conversion (%) | Selectivity (%) | Yield (%) | Turnover number |
|---|---|---|---|---|---|---|
| 1 | 10a | 100 | 14 | 74 | 10 | 1000 |
| 2 | 10b | 100 | 20 | 78 | 15 | 1500 |
| 3 | 10c | 100 | 6 | 86 | 5 | 550 |
| 4 | 10d | 100 | 26 | 82 | 22 | 2200 |
| 5 | 10e | 100 | 44 | 79 | 34 | 3400 |
| 6 | 10k | 100 | 7 | 91 | 6 | 600 |

The present inventors compared the activities of synthesized ruthenium complex catalysts with each other. The results of the activity analysis of the ruthenium complex catalysts represented by 10e to 10i having different structures are shown in Table 2.

The complex 10f with a sigma-donor functional group and tert-butyl functional group shows a higher conversion compared to the complex 10e. However, the complexes 10g and 10h with the pie-donor functional group shows the lower conversion. The complex 10i with chlorine group in R1 does not show activity.

Table 2 summarizes the backbone substitution effect of F-ImPy-Ru catalysts. The complex 10f containing the σ-donating t-Bu group in the backbone has 50% conversion and 4000 turnover number to improves the activity of the catalyst compared to the complex 10e (item 2 vs item 1).

However, the catalysts 10g and 10h exhibit the lower conversions (item 3 and 4 vs item 1) compared to the complex 10e. In the complexes 10g and 10h, the 71-donating group appears to be ineffective because it exhibits a low turnover number.

The Cl-ImPy-Ru catalyst does not exhibit catalyst activity (item 5).

The reaction conditions in the experiment in Table 2 were based on the catalyst content (ppm), and $C_2H_4$(150 psi, 99.95% purity). The conversion and selectivity at 60° C. for 3 hours were measured using tridecane as an internal standard and using GC.

The conversion is calculated as 100−[(final molar number 1)*100/[initial molar number 1]].

The selectivity is calculated as 100*(2+3 moles)/[(2+3 moles)+(2*4+5 moles)].

The yield is calculated as conversion*selectivity/100.

The turnover number is calculated as yield*(initial mole number 1/mole number of catalyst)/100.

TABLE 2

Electronic effect of backbone substituent in ImPy (10e-10i)

| Item | Catalyst | Loading (ppm) | Conversion (%) | Selectivity (%) | Yield (%) | Turnover number |
|---|---|---|---|---|---|---|
| 1 | 10e | 100 | 44 | 79 | 34 | 3400 |
| 2 | 10f | 100 | 51 | 77 | 39 | 4000 |
| 3 | 10g | 100 | 34 | 81 | 27 | 2700 |
| 4 | 10h | 100 | 27 | 83 | 23 | 2300 |
| 5 | 10i | 100 | <1 | — | — | — |

The present inventors compared the activity of the 10f ruthenium complex catalyst. The results of the activity analysis by controlling the amount of catalyst of the ruthenium complex catalyst indicated by 10f and the temperature are shown in Table 3.

We have established the reaction conditions by controlling the amount of catalyst of ruthenium complex catalyst having the 10f structure and temperature. Thus, 6700 TON (turnover numbers) was obtained at a temperature of 60° C. using a catalyst amount of 20 ppm.

Table 3 summarizes the optimization of the reaction condition for catalyst loading and reaction temperature. The catalyst loading at 60° C. and the 200 ppm shows optimum catalyst performance (6700 turnover number, 71% selectivity).

The reaction conditions in the experiment of Table 3 were based on the catalyst content (ppm), and $C_2H_4$(150 psi, 99.95% purity). The conversion and selectivity at 60° C. for 3 hours were measured using tridecane as an internal standard and using GC.

The conversion is calculated as 100−[(final molar number 1)*100/[initial molar number 1]].

The selectivity is calculated as 100*(2+3 moles)/[(2+3 moles)+(2*4+5 moles)].

The yield is calculated as conversion*selectivity/100.

The turnover number is calculated as yield*(initial mole number 1/mole number of catalyst)/100.

Item 5 of Table 3 refers to a reaction for 12 hours.

TABLE 3

Various catalyst loading and temperature effects on ethenolysis of 1 (MO)

| Item | Catalyst | Temperature (° C.) | Loading (ppm) | Conversion (%) | Selectivity (%) | Yield (%) | Turnover number |
|---|---|---|---|---|---|---|---|
| 1 | 10f | 60 | 200 | 68 | 79 | 54 | 2700 |
| 2 | | 60 | 100 | 51 | 77 | 39 | 3900 |

TABLE 3-continued

Various catalyst loading and temperature effects on ethenolysis of 1 (MO)

| Item | Catalyst | Temperature (° C.) | Loading (ppm) | Conversion (%) | Selectivity (%) | Yield (%) | Turnover number |
|---|---|---|---|---|---|---|---|
| 3 | | 60 | 50 | 32 | 77 | 25 | 5100 |
| 4 | | 60 | 20 | 19 | 71 | 13 | 6700 |
| 5 | | 40 | 100 | 25 | 77 | 19 | 1900 |
| 6 | | 80 | 100 | 55 | 76 | 42 | 4200 |
| 7 | | 100 | 100 | 57 | 72 | 41 | 4100 |

The present disclosure describes the synthesis of a novel ruthenium catalyst containing an asymmetric ImPy ligand (ImPy-Ru) and the application thereof to the catalytic ethenolysis of methyl oleate.

The effects of the ligand structure changes on the catalyst activity, selectivity and stability were investigated. The Ru—F interactions were identified using the solid state by X-ray analysis, and the Ru—F interactions could stabilize ruthenium methylidene intermediates.

The F-ImPy-Ru catalyst with an ortho-t-Bu-phenyl substituent on the ring nitrogen and a sigma donating t-Bu group on the pyridine backbone showed a high turnover number (up to 6700).

The ImPy-Ru catalyst exhibits the high selectivity (up to 86%) to the terminal olefin formation in the ethenolysis of methyl oleate.

The ruthenium complex according to [Chemical Formula 2a] and [Chemical Formula 2b] according to the present disclosure may be used as a catalyst in the olefin metathesis reaction. Thus, the production yield of the linear alpha-olefins through the olefin metathesis reaction can be improved.

That is, the ruthenium complex catalyst of the Present Example can exhibit selectivity of greater than 70% in the olefin metathesis reaction at 60° C. for 3 hours. For example, the ruthenium complex catalyst of the Present Example can exhibit selectivity of 75% to 86% to the terminal olefin formation in the ethenolysis of methyl oleate. For example, the ruthenium complex catalyst of the Present Example can exhibit 81% to 86% selectivity to terminal olefin formation in the ethenolysis of methyl oleate.

The ruthenium complex according to the present disclosure is not limited thereto, and may be utilized in various reactions such as an intramolecular ring-closing olefin metathesis reaction, an intermolecular olefin metathesis reaction, and an olefin metathesis polymerization reaction.

Figure 5:
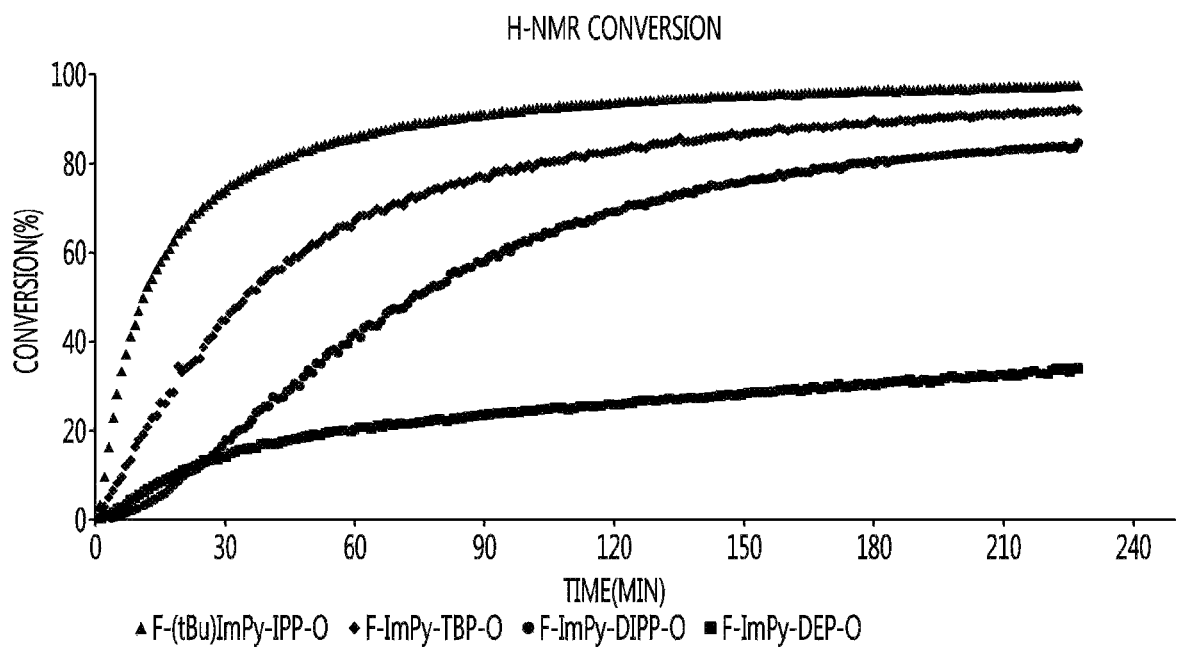
FIG. 5 is a graphical representation of a conversion observed in an intramolecular ring-closed metathesis reaction when using various ImPy-Ru complexes according to E example.

For example, referring to FIG. 5, the ruthenium complexes according to the present disclosure can form cyclic products with a high yield from linear reaction products via the intramolecular ring-closing metathesis reactions.

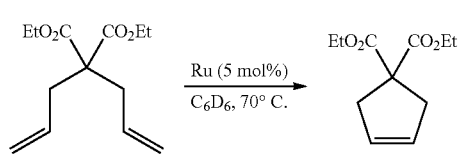

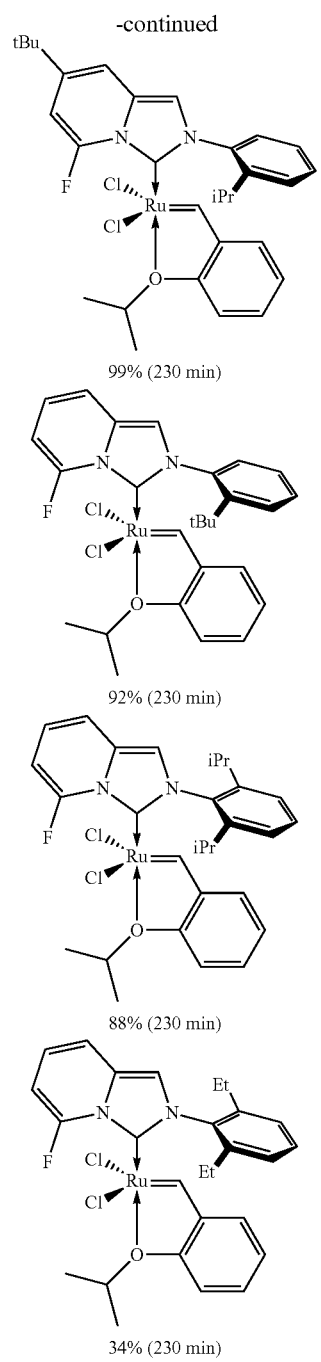

For example, when using the ImPy-Ru complex according to the Example, the conversion in the intramolecular ring-closed metathesis reaction may be greater than 88%. For example, in the case of using the ImPy-Ru complex according to the Example, the conversion in the intramolecular ring-closed metathesis reaction may be greater than 92%. For example, in the case of using the ImPy-Ru complex according to Example, the conversion in the intramolecular ring-closed metathesis reaction may be from 92% to 99%.

Figure 6:
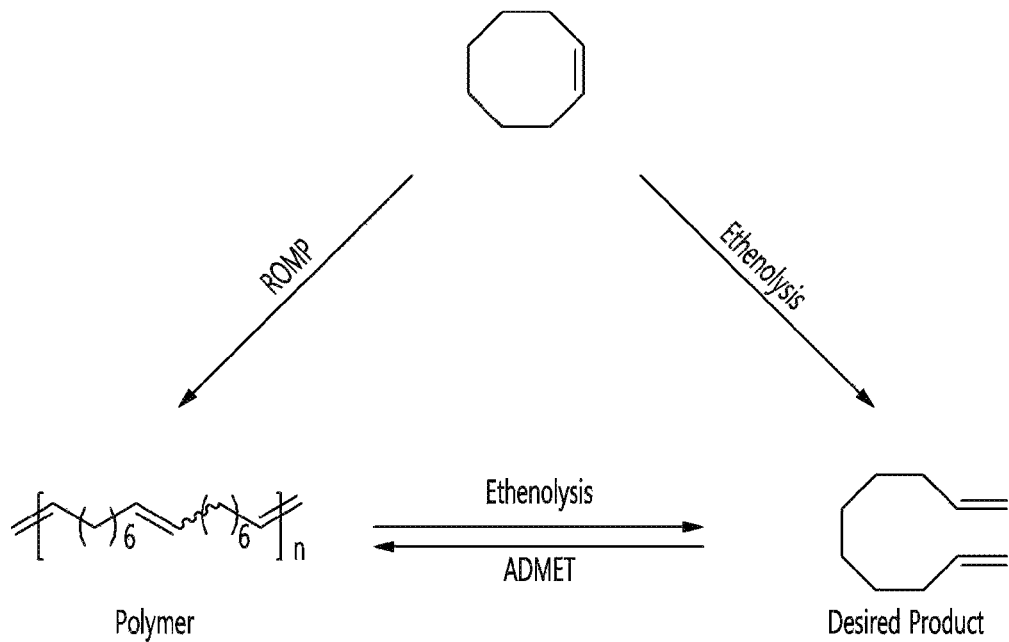
FIG. 6 illustrates a selective ethenolysis reaction for synthesis of cyclic alkyne compound and linear α, ω-diene as linear unsaturated polymer.

Referring to FIG. 6, the ruthenium complexes according to the present disclosure may be applied to the selective ethenolysis reaction for the synthesis of linear α, ω-diene of cyclic alkyne compounds. That is, linear α, ω-dienes can be synthesized through ethenolysis of cis-cyclooctene.

Table 4 summarizes optimization of reaction conditions for catalyst loading and reaction temperature. (73 conversion, 47% selectivity and 34% yield)

The reaction conditions in the experiments in Table 4 were based on the catalyst content (ppm), and $C_2H_4$(150 psi, 99.95% purity). The conversion and selectivity at 60° C. for 3 hours were measured using tridecane as an internal standard and using GC.

TABLE 4

Comparison of activity of 10f ruthenium complex catalyst

| Item | Loading (ppm) | Pressure (psi) | Conversion (%) | Selectivity (%) | Yield (%) | Turnover number |
|---|---|---|---|---|---|---|
| 1 | 100 | 150 | 70 | 22 | 15 | 1500 |
| 2 | 200 | 150 | 69 | 25 | 17 | 900 |
| 3 | 500 | 150 | 70 | 48 | 33 | 700 |
| 4 | 1000 | 150 | 73 | 47 | 34 | 700 |
| 5 | 500 | 200 | 68 | 48 | 33 | 700 |
| 6 | 500 | 300 | 60 | 56 | 34 | 700 |

In the ruthenium complex and cyclic alkyne compound reaction, the ring opening metathesis polymerization may have high activity and may allow competitive side reaction of ethenolysis.

In addition, linear α, ω-diene can be competitively side-reacted via condensation polymerization while ethylene is removed. For example, referring to FIG. 6, the ruthenium complex catalyst according to the present disclosure may allow synthesis of the diene polymers through the intermolecular olefin polymerization reaction from diene compounds having double bonds at each terminal of the linear compound. In this connection, n may be from several to several hundred. For example, n may be from 1 to 700. Alternatively, n may be from 10 to 500. Alternatively, n may be from 100 to 300. In this connection, the linear terminal diene compound may mean various compounds having from 4 to 20 carbon atoms. For example, the linear terminal diene compound may be selected from a group consisting of 1,9-decadiene, 1,8-nonadiene, 1,7-octadiene, 1,6-heptadiene, 1,5-hexadiene, 1,4-pentadiene and 1,3-butadiene.

For example, referring to FIG. 6, the ruthenium complex catalyst according to the present disclosure can be used to obtain a desired product, that is, the diene compound as a monomer having a double bond at each terminal of a linear compound from the linear diene polymer. That is, the ruthenium complex catalyst according to the present disclosure can be used in the depolymerization or ethenolysis reaction of an unsaturated linear polymer containing a double bond.

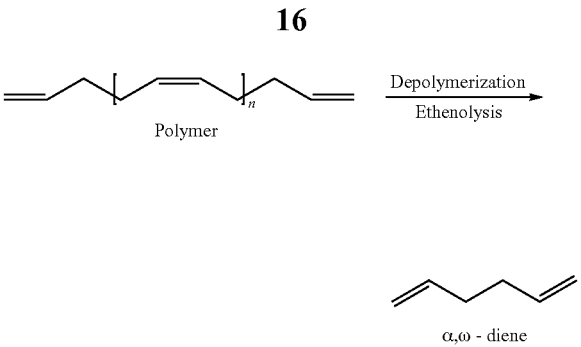

For example, the ruthenium complex catalyst according to the present disclosure may be used to improve the yield of the depolymerization or ethenolysis reaction of 1,4-polybutadiene.

For example, the ruthenium complex catalyst according to the present disclosure may be used to synthesize the linear diene compound such as 1,9-decadiene, 1,8-nonadiene, 1,7-octadiene, 1,6-heptadiene, 1,5-hexadiene, 1,4-pentadiene, and 1,3-butadiene using the depolymerization or ethenolysis reaction.

What is claimed is:

1. A ruthenium complex catalyst having a structure represented by a following Chemical Formula 2a:

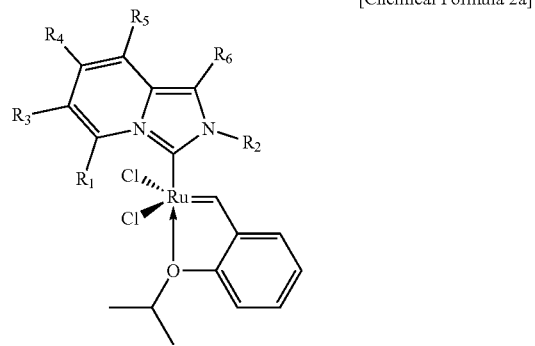

[Chemical Formula 2a]

wherein R1 comprises an atom or atomic group smaller than R2, wherein each of R3, R4, R5 and R6 is selected from the group consisting of hydrogen, a halogen atom, a linear or branched alkyl group having 1 to 5 carbon atoms, or an alkoxy group having 1 to 5 carbon atoms.

2. The ruthenium complex catalyst of claim 1, wherein R1 represents F or methyl, wherein R2 represents a substituted or unsubstituted aryl.

3. The ruthenium complex catalyst of claim 1, wherein R2 represents a substituted aryl of 9 to 12 carbon atoms.

4. The ruthenium complex catalyst of claim 1, wherein each of R3, R5, and R6 is hydrogen.

5. The ruthenium complex catalyst of claim 1, wherein R4 is one selected from the group consisting of H, t-Bu, MeO, and Cl.

6. The ruthenium complex catalyst of claim 1, wherein the ruthenium complex catalyst has a structure represented by a following Chemical Formula 2b:

[Chemical Formula 2b]

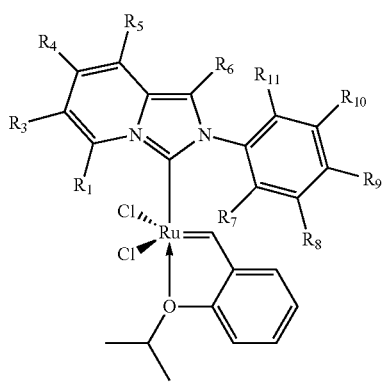

wherein each of R7, R8, R9, R10 and R11 is selected from the group consisting of hydrogen or a linear or branched alkyl group having 1 to 8 carbon atoms.

7. A process comprising carrying out an ethylene-based metathesis reaction of a linear or cyclic alkene compound comprising methyl oleate in the presence of the ruthenium complex catalyst according to claim 1.

8. A process according to claim 7 wherein the ethylene-based metathesis reaction includes an intramolecular cross-metathesis reaction, a ring-opening metathesis reaction, a ring-closing metathesis reaction, a ring-opening metathesis polymerization reaction, or an acyclic diene metathesis polymerization reaction.

9. A method for producing a ruthenium complex catalyst, the method comprising:
a first step of preparing a pyridine derivative;
a second step of forming a 2-fluoropyridine derivative by selective fluorination;
a third step of forming a fluoropyridine carboxaldehyde from the 2-fluoropyridine derivative;
a fourth step of forming an imine by reaction of the fluoropyridine carboxaldehyde with an aniline compound;
a fifth step of forming a ligand having a structure of a following Chemical Formula 1a by an intramolecular cyclization reaction of the imine with AgOTf and tBuCO$_2$CH$_2$Cl; and
a sixth step of binding the ligand to Ru to form a ruthenium complex catalyst having a structure of a following Chemical Formula 2a:

[Chemical Formula 1a]

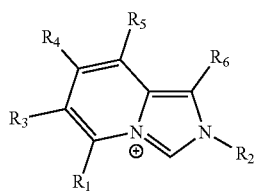

[Chemical Formula 2a]

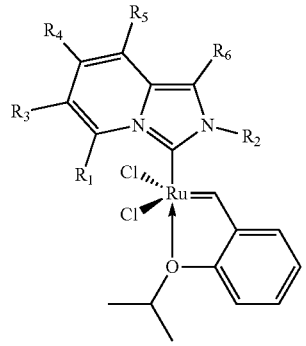

wherein R1 comprises an atom or atomic group smaller than R2, wherein each of R3, R4, R5 and R6 is selected from the group consisting of hydrogen, a halogen atom, a linear or branched alkyl group having 1 to 5 carbon atoms, or an alkoxy group having 1 to 5 carbon atoms.

10. The method of claim 9, wherein the second step includes selective fluorination with AgF$_2$ in CH$_3$CN.

11. The method of claim 9, wherein the third step includes obtaining the fluoropyridine carboxaldehyde by a reduction reaction of 2-pyridine carboxylate derivative with DIBAL-H reducing agent.

12. The method of claim 9, wherein the third step includes obtaining the fluoropyridine carboxaldehyde by n-BuLi, DMF treatment of 2-bromopyridine.

13. A ligand for ruthenium complex formation, the ligand having a structure represented by a following Chemical Formula 1a:

[Chemical Formula 1a]

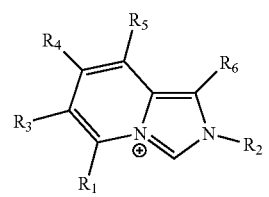

wherein R1 represents F or Cl,
wherein R2 represents MEP(2-methyl-6-ethylphenyl), DEP(2,6-diethylphenyl), DIPP(2,6-diisopropylphenyl), IPP(2-isopropylphenyl) or TBP(2-t-butylphenyl),
wherein each of R3, R5 and R6 represent hydrogen, and
wherein R4 represents t-Bu or Cl.

* * * * *